US012694967B2

(12) United States Patent
Monas et al.

(10) Patent No.: US 12,694,967 B2
(45) Date of Patent: Jul. 28, 2026

(54) MEDICAL SYSTEM FOR ESTABLISHING COMMUNICATION BETWEEN DEVICES USING CODE SCANNING

(71) Applicant: West Affum Holdings DAC, Dublin (IE)

(72) Inventors: Edmund Monas, San Antonio, TX (US); Angela M. Stewart, Kenmore, WA (US); Ronald E. Zahorka, Jr., Denver, CO (US); Jennifer D. Imerini, St. Augustine, FL (US); Justin Beurmann, Lake Orion, MI (US); Patrick Beighle, Seattle, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

(21) Appl. No.: 19/097,280

(22) Filed: Apr. 1, 2025

(65) Prior Publication Data

US 2025/0316360 A1    Oct. 9, 2025

Related U.S. Application Data

(60) Provisional application No. 63/574,533, filed on Apr. 4, 2024.

(51) Int. Cl.
| | |
|---|---|
| *G16H 20/40* | (2018.01) |
| *A61N 1/04* | (2006.01) |
| *A61N 1/39* | (2006.01) |
| *G16H 10/60* | (2018.01) |
| *G16H 40/67* | (2018.01) |

(52) U.S. Cl.
CPC .......... *G16H 20/40* (2018.01); *A61N 1/0484* (2013.01); *A61N 1/3993* (2013.01); *G16H 10/60* (2018.01); *G16H 40/67* (2018.01)

(58) Field of Classification Search
CPC ........ G16H 20/40; G16H 40/67; G16H 10/60; A61N 1/0484; A61N 1/3993
See application file for complete search history.

(56) References Cited

U.S. PATENT DOCUMENTS

| | | | |
|---|---|---|---|
| 7,756,573 B2 * | 7/2010 | Shen .................... | A61B 5/0031 600/509 |
| 8,521,269 B1 * | 8/2013 | Gunderson ........ | A61N 1/37247 600/518 |
| 11,089,958 B2 * | 8/2021 | Brisben ................. | A61B 5/363 |

(Continued)

*Primary Examiner* — Michael I Ezewoko
(74) *Attorney, Agent, or Firm* — Seed Intellectual Property Law Group LLP

(57)    ABSTRACT

A medical system including a wearable medical device configured to provide therapy to a patient upon detection of a cardiac condition, one or more remote servers, and a mobile device including at least one processor, a memory, a display, and a code reader. The at least one processor is configured to receive a code from the code reader, the code comprising a contact. The at least one processor is further configured to cause the contact to be stored in the memory of the mobile device by a contacts module of the mobile device based on the code. The contact includes contact data, which is associated with the one or more remote servers. The at least one processor is further configured to transmit an authorization to the one or more remote servers, and receive one or more communications at the mobile device from the one or more remote servers.

18 Claims, 4 Drawing Sheets

(56) References Cited

U.S. PATENT DOCUMENTS

| | | | | |
|---|---|---|---|---|
| 11,357,441 | B2 * | 6/2022 | Perschbacher | A61B 5/0006 |
| 11,491,337 | B2 * | 11/2022 | Mahajan | A61B 5/361 |
| 11,607,554 | B2 * | 3/2023 | Finch | A61N 1/3904 |
| 11,806,543 | B2 * | 11/2023 | Mahajan | A61B 5/316 |
| 12,383,749 | B2 * | 8/2025 | Mahajan | A61B 5/7475 |
| 12,434,065 | B2 * | 10/2025 | Mahajan | A61B 5/316 |
| 12,525,359 | B2 * | 1/2026 | Rajan | A61N 1/37235 |
| 2006/0247548 | A1 * | 11/2006 | Sarkar | A61B 5/363 |
| | | | | 600/515 |
| 2008/0058651 | A1 * | 3/2008 | Shen | A61N 1/3706 |
| | | | | 607/9 |
| 2010/0106036 | A1 * | 4/2010 | Dong | G09B 7/02 |
| | | | | 434/262 |
| 2012/0190969 | A1 * | 7/2012 | Kameli | A61N 1/39624 |
| | | | | 607/29 |
| 2013/0085403 | A1 * | 4/2013 | Gunderson | A61B 5/339 |
| | | | | 600/510 |
| 2013/0211855 | A1 * | 8/2013 | Eberle | A61B 5/0022 |
| | | | | 600/529 |
| 2016/0045125 | A1 * | 2/2016 | Krueger | A61B 5/02405 |
| | | | | 600/518 |
| 2016/0278659 | A1 * | 9/2016 | Kaib | A61B 5/35 |
| 2017/0196457 | A1 * | 7/2017 | Thakur | A61B 5/0205 |
| 2017/0281095 | A1 * | 10/2017 | An | G16H 40/63 |
| 2017/0290550 | A1 * | 10/2017 | Perschbacher | A61B 5/076 |
| 2018/0064360 | A1 * | 3/2018 | Siejko | A61B 5/349 |
| 2018/0104502 | A1 * | 4/2018 | Perschbacher | A61B 5/7264 |
| 2018/0192902 | A1 * | 7/2018 | Perschbacher | A61B 5/361 |
| 2019/0008384 | A1 * | 1/2019 | Brisben | A61B 5/364 |
| 2019/0231207 | A1 * | 8/2019 | Perschbacher | A61B 5/0006 |
| 2019/0232067 | A1 * | 8/2019 | Mahajan | A61B 5/361 |
| 2020/0016420 | A1 * | 1/2020 | Mahajan | A61B 5/316 |
| 2021/0338168 | A1 * | 11/2021 | Landman | A61B 5/364 |
| 2022/0280095 | A1 * | 9/2022 | Perschbacher | A61B 5/0006 |
| 2024/0017081 | A1 * | 1/2024 | Mahajan | A61B 5/316 |
| 2025/0049374 | A1 * | 2/2025 | Siejko | A61B 5/364 |

* cited by examiner

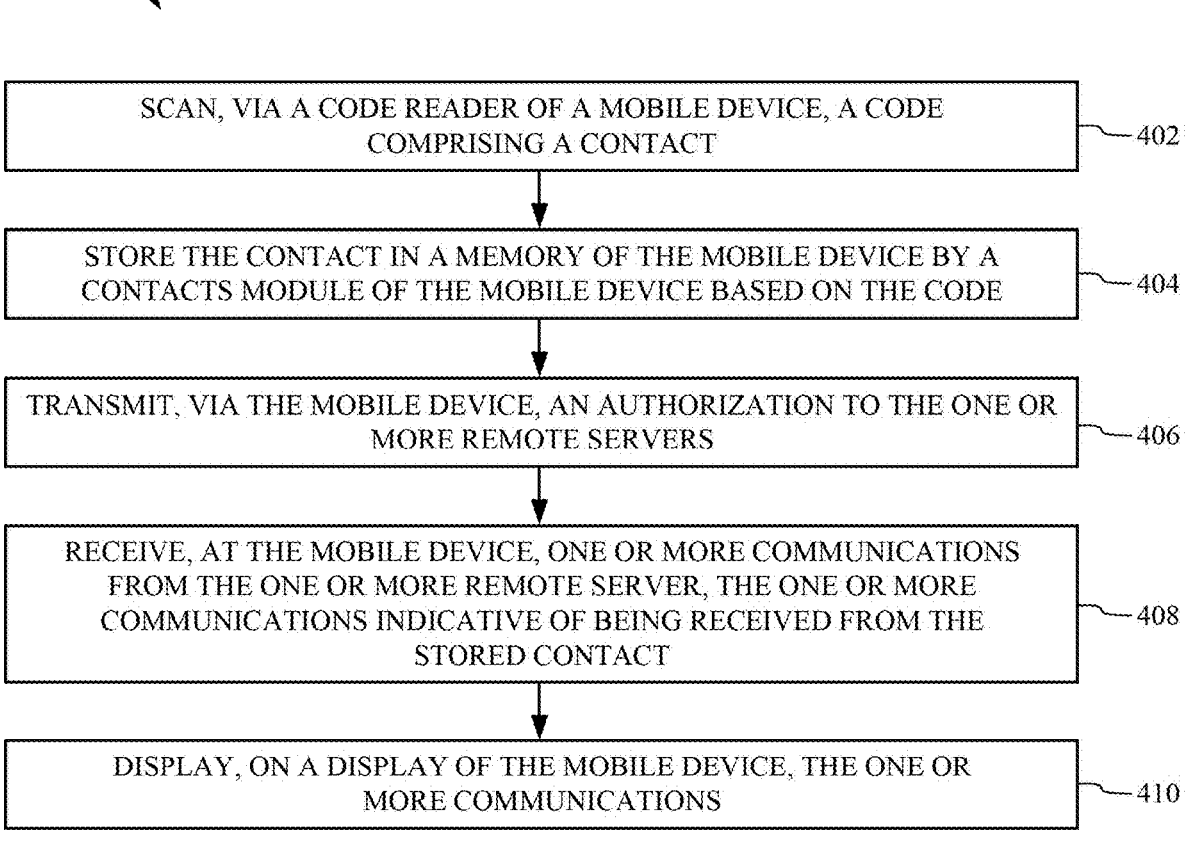

400

SCAN, VIA A CODE READER OF A MOBILE DEVICE, A CODE COMPRISING A CONTACT — 402

STORE THE CONTACT IN A MEMORY OF THE MOBILE DEVICE BY A CONTACTS MODULE OF THE MOBILE DEVICE BASED ON THE CODE — 404

TRANSMIT, VIA THE MOBILE DEVICE, AN AUTHORIZATION TO THE ONE OR MORE REMOTE SERVERS — 406

RECEIVE, AT THE MOBILE DEVICE, ONE OR MORE COMMUNICATIONS FROM THE ONE OR MORE REMOTE SERVER, THE ONE OR MORE COMMUNICATIONS INDICATIVE OF BEING RECEIVED FROM THE STORED CONTACT — 408

DISPLAY, ON A DISPLAY OF THE MOBILE DEVICE, THE ONE OR MORE COMMUNICATIONS — 410

FIG. 4

MEDICAL SYSTEM FOR ESTABLISHING COMMUNICATION BETWEEN DEVICES USING CODE SCANNING

CROSS-REFERENCE TO RELATED APPLICATIONS

This application claims priority to and the benefit of the provisional patent application No. 63/574,533 titled "QR CODE FOR PATIENT SMS", filed in the United States Patent and Trademark Office on Apr. 4, 2024. The specification of the above referenced patent application is incorporated herein by reference in its entirety.

TECHNICAL FIELD

The present technology relates to the field of wearable medical systems and more particularly, but not by way of limiting, the present technology relates to a medical system that uses code scanning, such as Quick Response (QR) codes, to facilitate the establishment of communication between multiple devices in the medical system, allowing patient(s) to receive authorized text messages from a wearable medical device (WMD) provider by creating the WMD provider as a contact in the patient's mobile device.

BACKGROUND

Wearable medical devices (WMDs) are devices used to monitor and treat patients with cardiac conditions. These devices are often paired with mobile devices to transmit patient data to remote servers for continuous monitoring and analysis. While the pairing is effective in improving patient care, many patients encounter challenges in engaging with the medical system, particularly in terms of communication with a provider of the WMD.

One of the common issues that arises in such systems is that patients often fail to recognize or respond to messages sent by the WMD provider, particularly when the messages are sent from an unrecognized phone number. When patients receive text messages or notifications from unknown numbers, they may dismiss these messages as spam or overlook them entirely. This is especially problematic for critical communications, such as alerts or instructions from the healthcare provider. If patients ignore or fail to notice these messages, it can result in missed opportunities for important interactions, such as reminders for therapy or follow-up care.

Additionally, the process of setting up the communication system between the wearable medical device and the patient's mobile device can often be confusing and cumbersome. For instance, patients may struggle to properly configure their devices, associate contacts, or grant necessary permissions to receive texts. These challenges are exacerbated for individuals with limited technical expertise, creating an unnecessary barrier to efficient communication and patient care. Furthermore, obtaining patient consent to receive text messages or other forms of communication is typically a tedious and time-consuming process that is not always user-friendly.

Current solutions, such as sending text messages from unrecognized numbers, attempt to address the need for communication but inadvertently create confusion and inefficiencies. While some systems may include manual setup or verification steps, these processes often fall short in ensuring patients correctly receive, recognize, and engage with critical messages. As a result, there is a need for improvements that can facilitate easier communication, ensure messages are not ignored, and streamline the setup process for patients receiving important messages from their WMD providers.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure relates to a medical system that establishes communication between multiple devices using code scanning. In one aspect of the present disclosure, the medical system includes a wearable medical device, one or more remote servers, and a mobile device. The wearable medical device is configured to provide therapy to a patient upon detection of a cardiac condition based on patient data. The mobile device includes at least one processor, a memory, a display, and a code reader, and is in communication with the one or more remote servers and the wearable medical device.

The at least one processor is configured to receive a code from the code reader, the code including a contact. The at least one processor is further configured to cause the contact to be stored in the memory of the mobile device by a contacts module of the mobile device based on the code. The contact includes contact data, which is associated with the one or more remote servers. Additionally, the at least one processor is configured to transmit an authorization to the one or more remote servers, and in response to transmitting the authorization, the at least one processor is configured to receive one or more communications at the mobile device. The one or more communications are indicative of being received from the contact stored in the memory of the mobile device. The authorization may be transmitted to the one or more remote servers by medical personnel using a medical personnel device. In some embodiments, the one or more communications may include a welcome message displayed on the display with the contact data. Additionally, the one or more communications may include training programs, patient data, physician messages, and other communications associated with the wearable medical device. The code is a Quick response (QR) code.

The at least one processor is further configured to display an authorization form, receive one or more user inputs associated with the authorization form, and transmit the authorization form to the one or more remote servers. The medical system further includes one or more additional mobile devices associated with one or more patient caregivers. The one or more additional mobile devices include at least one processor, a memory, a display, and a code reader. The at least one processor of the one or more additional mobile devices is configured to receive the code from the code reader and cause the contact to be stored in the memory of the one or more additional mobile devices by a contacts module of the one or more additional mobile devices based on the code. The at least one processor of the one or more additional mobile devices is configured to receive the one or more communications in response to transmitting an authorization for the one or more additional mobile devices to the one or more remote servers.

BRIEF DESCRIPTION OF THE DRAWINGS

The above-mentioned implementations are further described herein with reference to the accompanying figures. It should be noted that the description and figures relate to exemplary implementations and should not be construed as a limitation to the present disclosure. It is also to be understood that various arrangements may be devised that, although not explicitly described or shown herein, embody the principles of the present disclosure. Moreover, all statements herein reciting principles, aspects, and embodiments of the present disclosure, as well as specific examples, are intended to encompass equivalents thereof.

FIG. 4 illustrates an example method for establishing communication between a wearable medical device (WMD) worn by a patient, a mobile device, and one or more remote servers, in accordance with an embodiment of the present disclosure.

DETAILED DESCRIPTION

Figure 1:
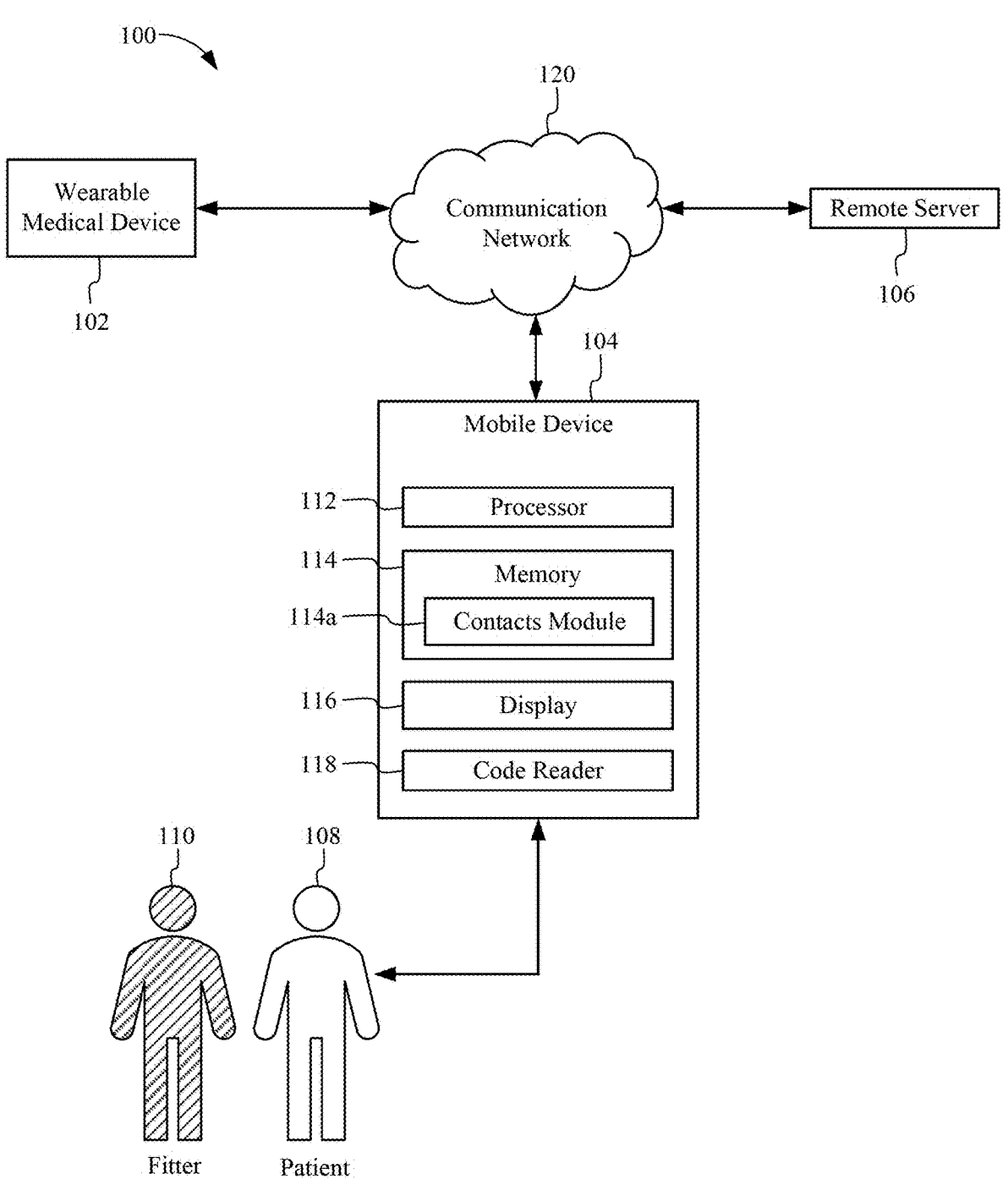
FIG. 1 depicts components of a medical system along with the connections therebetween for establishing communication between devices, according to an embodiment of the present disclosure.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures or methods associated with the wearable medical system have not been shown or described in detail to avoid unnecessarily obscuring descriptions of the embodiments.

Unless the context indicates otherwise, throughout the specification and claims which follow, the word "comprise" and variations thereof, such as, "comprises" and "comprising" are to be construed in an open, inclusive sense that is as "including, but not limited to." Further, the terms "first," "second," and similar indicators of the sequence are to be construed as interchangeable unless the context clearly dictates otherwise.

Reference throughout this specification to "one aspect" or "an aspect" means that a particular feature, structure, or characteristic described in connection with an embodiment is included in at least one aspect. Thus, the appearances of the phrases "in one aspect" or "in an aspect" in various places throughout this specification are not necessarily all referring to the same embodiment. Furthermore, the particular features, structures, or characteristics may be combined in any suitable manner in one or more aspects.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

Certain terms and phrases have been used throughout the disclosure and will have the following meanings in the context of the ongoing disclosure:

The term "wearable medical device" refers to a medical device worn by a patient, designed to monitor, detect, or provide therapeutic intervention for specific medical conditions. In the context of the present disclosure, the wearable medical device is configured to detect cardiac conditions of a patient based on physiological data and may provide necessary therapy, such as electrical stimulation or pacing upon detecting a medical condition (e.g., arrhythmia). The wearable medical device works in conjunction with a mobile device to ensure continuous patient monitoring and efficient data exchange to facilitate treatment, when needed.

The term "mobile device" refers to a portable, handheld electronic device that enables interaction with the wearable medical device and a remote server. The mobile device includes hardware components such as a processor, memory, display, and code reader, which allow the patient to scan a code containing contact data corresponding to a contact, store the data in memory, and communicate with the remote server. The contact data may be encoded in a code, such as the Quick response (QR) code, which can be scanned by the mobile device. Additionally, the mobile device facilitates storing of the contact data, receiving communications from the remote server to improve usage of the wearable medical device by a patient, and displaying relevant information, including welcome messages, training programs, or other patient-related communications.

The term "code reader" refers to a component of the mobile device capable of scanning and interpreting a code, such as the QR code. The code encodes the contact data, such as but not limited to a name and phone number corresponding to the contact, and is used to establish a link between the mobile device and the medical system. Upon scanning the code, the code reader enables efficient transmission of the contact data to the mobile device, which can be stored and used for authorized communications between the patient, caregivers, and the remote server.

The term "remote server" refers to a computer system or network server responsible for managing patient data and communications. The remote server interacts with the mobile device to receive authorization and send communications, such as welcome messages, patient data, or training programs, back to the mobile device. While the contact data (such as the device maker's name and phone number) is stored on the mobile device, the remote server facilitates communication between the patient, caregivers, and medical personnel, ensuring that sensitive patient data is properly handled and securely transmitted as needed. The remote server, in some embodiments, may be configured to store patient data and/or associated contact data to perform the intended communication-related tasks.

The term "authorization" refers to a process where individuals or medical personnel provide consent for certain actions or communications to be carried out by the mobile device or the remote server. The authorization ensures that the patient data, including the contact data and sensitive medical information, is only accessed and transmitted with appropriate approval. Authorization can be granted by the patient through user input on the mobile device or transmitted through the medical personnel's device to the remote server.

The embodiments of the present disclosure relate to a medical system designed to improve patient engagement and facilitate efficient communication between patients, mobile devices, and remote servers. In particular, the WMD system allows patients to scan the QR code to store a contact of the provider of the WMD, and opt into receiving text messages from a remote server or cloud service (e.g., the WMD provider's server and/or Salesforce). The QR code also automatically adds the WMD provider as a contact in the patient's mobile device, ensuring that future communications from the provider are easily recognized. The medical system ensures that mobile devices receive authorized communications from the remote server, including welcome messages, patient data, or other relevant information, providing a seamless experience for the patient and caregivers. The medical system aims to optimize the interaction between the wearable medical device, the mobile device, and the remote servers to ensure continuous engagement and timely updates.

Additionally, the medical system is configured to address potential delays in communication, especially during life-threatening situations such as cardiac events. When the patient's wearable medical device detects an abnormal cardiac condition, the medical system ensures that relevant patient data is immediately communicated to one or more remote servers via a mobile device, allowing medical professionals to act quickly.

FIG. 1 depicts components of a medical system 100 along with the connections therebetween for establishing communication between multiple devices, in accordance with an embodiment of the present disclosure. The medical system 100 includes a wearable medical device (WMD) 102, a mobile device 104, a remote server 106, a patient 108, a fitter 110, and a communication network 120. As shown in FIG. 1, the mobile device 104 includes at least one processor 112, a memory 114, a display 116, and a code reader 118. Additionally, the memory 114 of the mobile device 104 may include a contacts module 114a. Further, for the sake of brevity, the remote server 106 is indicated as a single remote server 106 in FIG. 1, however there may be multiple remote servers, either at same geographical location or at different geographical locations operating and coordinating in a distributed manner to achieve server functionality, without limitation. Depending on the context, "remote server" and "one or more remote servers" are being used in the present disclosure. Similarly, depending on the context, "the processor" and "at least one processor" are being used in the present disclosure.

In some embodiments, the patient 108 may be a user, also known as a wearer of the WMD 102. Additionally, the patient 108 may be an individual who wears the WMD 102. Depending on the context, the WMD 102 may be interchangeably used as wearable cardioverter defibrillator (WCD) 102. In some embodiments, the WMD 102 may be an ASSURE WMD provided by Kestra Medical Technologies Inc., Kirkland WA (Kestra), but in other embodiments the WMD 102 can be provided by other companies. So, while the following description references Kestra as the WMD provider, other embodiments are not limited to using Kestra as the WMD provider. In embodiments, the WMD 102 and mobile device 104 are similar to those described in U.S. Pat. No. 8,838,235, U.S. patent Ser. No. 11/235,143, U.S. patent Ser. No. 11/794,005, and U.S. patent Ser. No. 11/950,174, all of which are incorporated by reference herein for all purposes.

In some embodiments, the WMD 102 may monitor physiological parameters associated with the patient 108. The physiological parameters may be measured to monitor cardiac health of the patient 108. The patient 108 may interact with the mobile device 104 to view real-time patient data based on the physiological parameters. The patient 108 may further receive alerts or notifications, and interact with medical professionals using the mobile device 104.

In some embodiments, the mobile device 104 may be operated through the communication network 120. The communication network 120 is a network that allows transmission of data and communications between the components of the medical system 100, including the wearable medical device 102, the mobile device 104, the remote server 106, and other relevant devices. Specifically, the communication network 120 may allow transmission of the patient data, including real-time physiological parameters from the WMD 102, for review and monitoring. Additionally, the communication network 120 may support the transfer of communications from the remote server 106, such as authorized text messages, alerts, and notifications, ensuring that the patient 108 receives important information in a timely manner. The communication network 120, without limitation, may be any communication network, such as but not limited to the Internet, an intranet, and the like.

In an exemplary embodiment, the remote server 106 may be a customer relation management (CRM) system such as the Salesforce CRM platform (Salesforce) available from Salesforce, Inc., San Francisco, CA with a Patient Messaging Module (not shown) and/or a server provided by the provider of the WMD 102 such as the Kestra CareStation remote data platform with a Patient Verification Module (not shown). In some embodiments, the Patient Messaging Module of the CRM system may be configured to communicate with the patient 108 using Short Message Service (SMS) or other messaging technologies. Additionally, the Patient Verification Module of the Kestra CareStation remote data platform may be configured to verify that the patient 108 is entered properly into the Kestra CareStation remote data platform. The verification of the patient 108 may include adding the patient 108 to a "holding clinic" when a physician is yet to be determined for the patient 108. In general, the "holding clinic" may refer to a virtual or temporary status within the remote server 106 to place the patient 108 in a waiting state while a healthcare provider or a physician is identified or assigned to the patient 108. Further, the Kestra CareStation remote data platform may be configured to communicate the received authorization to the Salesforce CRM platform upon the verification of the patient 108. The Salesforce CRM platform may further be configured to respond with a "welcome message" to the patient 108 as described in FIG. 2 later.

Without departing from the scope of the present disclosure, in some embodiments, the role of the remote server 106 may be performed by different elements, based on the functionality to be executed. For example, as described, messaging functionality may be executed by the Patient Messaging Module residing in a first element (e.g., the Salesforce CRM platform) while patient verification may be executed by the Patient Verification Module residing in a second element (e.g., Kestra CareStation platform). However, in other embodiments, a single element may perform different functionalities of the remote server 106 without limitation.

While the following description references Salesforce and the Kestra CareStation platform, the remote server 106 is not limited to Salesforce and/or the Kestra CareStation platform and may be implemented using one or more other platforms including server(s) and/or cloud-based services provided by the provider of the WMD 102.

The fitter 110 may assist the patient 108 in learning how to wear and use the WMD 102. The fitter 110 may ensure that the WMD 102 is correctly positioned on the body of the patient 108 in order to facilitate accurate monitoring of the physiological parameters of the patient 108. Additionally, the fitter 110 may help the patient 108 to understand the functions and capabilities of the WMD 102. The fitter 110 may further offer guidance to the patient 108 on proper usage of the WMD 102. For example, the fitter 110 may assist the patient 108 in learning features such as, any of, but not limited to, how to charge the WMD 102, interpret the patient data displayed on the mobile device 104, and troubleshoot issues associated with the medical system 100.

Additionally, the fitter 110 may guide the patient 108 in configuring settings on the mobile device 104. The fitter 110 may ensure that the mobile device 104 is paired with the WMD 102 for seamless synchronization of the patient data with the mobile device 104. The fitter 110 may also assist the patient 108 with installing necessary applications on the mobile device 104, such as but not limited to an application such as ASSURE Patient Application. In an example, the application may be Field Service Lightning (FSL) available from Salesforce. FSL may offer a mobile interface that allows field technicians to access customer information, view schedules, and update service status related to the patient 108. The fitter 110 may further offer training on how to use the application for monitoring health data, receiving notifications, and communicating with healthcare providers. The application may include other functionality, such as providing access to a user manual of the WMD 102, training, WMD wear time, patient activity monitoring (e.g., step counts). As part of the above-mentioned process, the fitter 110 may ask the patient 108 whether the patient 108 wants to receive texts on the mobile device 104 from the remote server 106. Upon receiving consent from the patient 108, the fitter 110 may assist the patient 108 in scanning the QR code to create a "Kestra" contact as described above. In some embodiments, the mobile device 104 may include a QR code module which may scan and process the QR code to create the Kestra contact in the mobile device 104. In some embodiments, the fitter 110 may display the QR code (e.g., using the tablet, FSL, a physical card, and the like) and ask the patient 108 to scan the QR code to create a contact (e.g., "Kestra") in the patient's mobile device 104. In other embodiments, the patient 108 may manually enter phone number into the application or service for creation of the contact. The new contact may be created in the mobile device 104 with a phone number from which text messages may be sent by the remote server 106 (e.g., Salesforce CRM platform). In this way, any subsequent texts received from the Salesforce CRM platform may be identified as legitimate as being received from Kestra so that the patient 108 is aware that the text messages are not spam or scam texts.

In some embodiments, the fitter 110 may follow a plurality of predefined steps in the application to set up the medical system 100. The plurality of pre-defined steps are detailed as set forth. At step one, the fitter 110 may prepare the patient 108 for a session of fitment of the WMD 102 according to the above embodiments. During the fitment session, the mobile device 104 may run an application (e.g., ASSURE application). The fitter 110 may further be required to record a patient code associated with the patient 108. The patient code may be maintained at the remote server 106 to uniquely identify each patient.

At step two, the fitter 110 may perform physical measurements of the patient 108 including, but not limited to, measurement of the patient 108 under bust circumference over light clothing for the fitment of the WMD 102. For the measurement of the patient 108, the fitter 110 may ensure that a measuring tape is wrapped tightly around the patient's rib cage at the lower border of sternum. The fitter 110 may take the measurements of the patient 108 to a nearest half-inch and round the measurements to the nearest half-inch. Based on the physical measurements of the patient 108, the fitter 110 may select a garment with appropriate size for the patient 108. The garment may refer to a wearable item designed to be worn by the patient 108, intended for monitoring and supporting the functioning of the WMD 102. The garment may be worn similarly to parallel articles of clothing. Additionally, the garment may be equipped with one or more sensors to monitor the physiological parameters and facilitate interaction with the medical system 100. The garment may be designed for proper fit and comfort, ensuring accurate sensor contact with the patient's skin. The garment may include features such as but not limited to one or more adjustable closures, straps, and a front pocket. Additionally, the garment may be constructed to securely hold a monitor and a battery, and may be compatible with various training and usage instructions, including those related to system alerts, charging, and maintenance.

In an example, if the measurement of the patient 108 falls in between two sizes (a smaller size and a larger size) of the garment, the fitter 110 may attempt to fit the patient 108 with the smaller-sized garment. In another example, if the measurement of the patient 108 falls outside a size range (for instance, less than 28 inches or more than 52 inches), the fitter 110 may not fit the patient 108 with the garment.

At step three, the fitter 110 may introduce a system kit associated with the medical system 100 to the patient 108. The fitter 110 may assure the patient 108 that that the patient 108 is taught usage of the medical system 100. At step four, the fitter 110 may ask the patient 108 to watch a training video. The patient 108 may be allowed to pause the training video for any comments or questions regarding the training video.

At step five, the fitter 110 may ask the patient 108 to assemble the garment. During the assembling of the garment, the fitter 110 may train the patient 108 in inserting and removing a hub associated with the garment. The fitter 110 may further familiarize the patient 108 with a wearable defibrillator patient handbook. In an example, the wearable defibrillator patient handbook may include but not limited to ASSURE Wearable Defibrillator Patient Handbook.

At step six, the fitter 110 may ask the patient 108 to wear the garment and place a battery in a monitor fixed with the garment. The fitter 110 may further ask the patient 108 to press an 'alert' button when an alert button icon appears. The 'alert' button may allow the patient 108 to manually trigger an alert, notifying medical professionals or caregivers of a potential issue or emergency, ensuring timely intervention if necessary. At step seven, the fitter 110 may connect a tablet to the monitor fixed with the garment. At step eight, the fitter 110 may ask the patient 108 to put on a carry pack and insert the monitor. At step nine, the fitter 110 may confirm programming of the medical system 100 and check fit of the garment. During this step, the fitter 110 may confirm if the settings of the WMD 102 are programmed according to a predefined prescription.

The fitter 110 may further check and confirm if the one or more sensors placed on the garment are making good contact with the skin of the patient 108. Furthermore, the fitter 110 may adjust the garment so that the one or more sensors are flat and touching bare skin of the patient 108. Additionally, the fitter 110 may check that the garment is not twisted, and no obstruction is present under the garment. Further, the fitter 110 may moisten the skin under the one or more sensors with water or lotion, and tighten the garment by adjusting one or more front closure snaps and shoulder straps of the garment for proper monitoring of the physiological parameters.

At step ten, the fitter 110 may create a report for the fitment session prior to exiting the application. At step eleven, the fitter 110 may train the patient 108 on wearing the medical system 100 during a normal day. The fitter 110 may inform the patient 108 about how to charge the battery using a charger. The fitter 110 may further teach the patient 108 to review where to place the monitor while sleeping, discuss required actions before and after taking a bath or shower, and review the garment washing instructions.

At step twelve, the fitter 110 may train the patient 108 on alerts using the ASSURE wearable defibrillator patient handbook, the training video, and a wearable defibrillator quick start guide. The fitter 110 may discuss what the patient 108 should do if a shock alert occurs and have a practice session with the patient 108 for pressing the alert button. In some embodiments, a shock may correspond to discharge of electric charge to restart the heart of the patient 108 when a cardiac condition is detected. The fitter 110 may discuss what the patient 108 should do if a system alert occurs. The fitter 110 may further discuss skin moisturizing procedures with the patient 108 to resolve garment-related system alerts.

At step thirteen, the fitter 110 may encourage the patient 108 to have one or more patient caregivers or family members read the ASSURE wearable defibrillator patient handbook. At step fourteen, the fitter 110 may complete a patient information card and insert the patient information card into a front pocket of the garment. At step fifteen, the fitter 110 may administer the patient 108 for a patient comprehension test. In the patient comprehension test, the patient 108 may be taught one or more pre-requisites to run the medical system 100. The one or more pre-requisites may include pressing the alert button to cancel the shock when the patient 108 gets a heart alert. The patient 108 may be aware that the medical system 100 would deliver the shock if there is a heart alert going unnoticed by the patient 108 while sleeping. The one or more pre-requisites may further include viewing the monitor and responding to the heart alert by pressing the alert button to fix a problem in case of the system alert. The one or more pre-requisites may further include wearing the medical system 100 all the time except when taking a bath, shower, or swim, ensuring that the battery in the monitor is changed every day and making sure that the garment snugs around the rib cage of the patient 108.

The fitter 110 may also be responsible for ensuring that the patient 108 receives support services through the mobile device 104. In some embodiments, the fitter 110 may upload documentation, such as but not limited to consent forms or patient information, to the remote server 106 to facilitate communication and take further actions between the patient 108, the fitter 110, and a healthcare team.

In some embodiments, the physiological parameters monitored by the WMD 102 may include but are not limited to heart rate, blood pressure, or other vital health signs. The WMD 102 may be configured to detect deviations from normal physiological ranges of the patient 108. The deviations may detect a cardiac condition faced by the patient 108. The WMD 102 may further be configured to transmit the patient data corresponding to the physiological parameters to the mobile device 104 once the cardiac condition is detected. The WMD 102 may further be configured to provide therapy to the patient 108 upon detection of the cardiac condition of the patient 108 based on the patient data.

In some embodiments, the WMD 102 may include a support structure configured to be worn by the patient 108, and monitoring electrodes and therapy electrodes to facilitate the detection and treatment of cardiac conditions faced by the patient 108. The monitoring electrodes are configured to continuously monitor the physiological parameters of the patient 108 by making electrical contact with the skin of the patient 108. Upon detection of a cardiac arrhythmia or other abnormality, the therapy electrodes, which may also be integrated into the support structure and positioned on the patient 108, are activated. The therapy electrodes are capable of delivering therapy in the form of electric shocks or pacing pulses to the patient's body. The therapy electrodes work in communication with an energy source and a processor, which are responsible for determining when the therapy should be administered to the patient 108. The therapy, typically delivered as transcutaneous pacing pulses or defibrillation shocks, aims to restore a normal heart rhythm by delivering electrical energy to the heart. The electrical shock, also referred to as a therapy shock, is intended to correct life-threatening arrhythmias, such as ventricular fibrillation or tachycardia, by momentarily halting the abnormal heart rhythm and allowing the heart to resume its normal rhythm. The therapy electrodes are positioned on the patient 108 to ensure optimal electrical contact with the skin for effective delivery of the shock or pacing pulses. In some embodiments, the WMD 102 may deliver a series of pacing pulses before a more significant defibrillation shock is administered, depending on the severity of the detected arrhythmia. This multi-step approach allows for tailored therapy, aiming to provide the most effective intervention for the patient's condition. In some embodiments, the mobile device 104 may be in communication with the WMD 102 and the remote server 106. The at least one processor 112 of the mobile device 104 may allow the fitter 110 to communicate with the WMD 102 and further receive the one or more communications from the remote server 106. The one or more communications (e.g., training instructions) cause improvement in the patient's ability to use the WMD 102. By receiving and understanding the training instructions, the patient 108 may become better equipped to operate the WMD 102 more efficiently. In some embodiments, the at least one processor 112 may be implemented in several ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on. The at least one processor 112 may include, or have access to, a non-transitory storage medium, such as memory 114.

The memory 114 may be implemented in a number of ways. Such ways include, by way of example and not of limitation, volatile memories, Non-volatile Memories (NVM), Read Only Memories (ROM), Random Access Memories (RAM), magnetic disk storage media, optical storage media, smart cards, flash memory devices, any combination of these, and so on. The memory 114 is thus a non-transitory storage medium. The memory 114, if provided, can include programs for the at least one processor 112, which the at least one processor 112 may be able to read and execute. More particularly, the programs can include sets of instructions in the form of code, which the at least one processor 112 may be able to execute upon reading. The programs may also include other information such as configuration data, profiles, scheduling, and the like that can be acted upon by the instructions. Executing is performed by physical manipulations of physical quantities, and may result in functions, operations, processes, acts, actions, and/ or methods to be performed, and/or the at least one processor 112 to cause other devices or components or blocks to perform such functions, operations, processes, acts, actions, and/or methods. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in the present disclosure.

In some embodiments, the at least one processor 112 may be configured to receive a code from the code reader 118, which may be configured to scan and interpret the code associated with code data. In an alternate embodiment, the code may physically be provided to the patient 108 by the fitter 110. The at least one processor 112 may further process the code data for communication or configuration of the medical system 100. In an example, the code is QR code, which is a two-dimensional barcode that may store a variety of information in a compact machine-readable format.

In some embodiments, at least one processor 112 may decode the variety of information contained within the QR code. Additionally, the code may include the contact. The contact may further include the contact data. The contact data may include information associated with contacting the provider or maker of the WMD 102. In an example, the contact data may include at least a name associated with a phone number. In general, the phone number may be a string of characters representing a telephone number. The phone number may vary in format and length depending on the country or region and may include additional components such as country codes, area codes, and extension numbers. In an example, the phone number may be in the format of a traditional 7 or 10-digit number. In another example, the phone number may be an international number that includes a "+" symbol followed by the country code, area code, and local number, and may also include an extension. In some embodiments, the phone number may be defined as any alphanumeric string that can be used for communication, including traditional phone numbers, Voice over IP (VoIP) identifiers, or other forms of digital communication addresses. The mobile device 104 and the remote server 106 may be capable of processing and storing the phone number in a flexible format to ensure that communication may occur across a variety of systems and regions, without being limited by a fixed number of digits.

Further, at least the name of the contact data may be associated with any of, but not limited to, a healthcare provider, support staff, or any individual necessary for communication related to the patient care or the WMD 102. Furthermore, the at least one processor 112 may store the captured contact data in the memory 114, where the contact data may be accessed or used later for communication purposes. The contact data may also be linked to a patient's profile or relevant medical records, ensuring that all interactions in the medical system 100 are properly tracked and managed. For example, the contact may be used to facilitate direct communication between the patient 108 and a healthcare professional or to enable notifications related to the WMD 102.

In some embodiments, the at least one processor 112 may be configured to cause the contact to be stored in the memory 114 of the mobile device 104 by the contacts module 114*a*. The contacts module 114*a*, associated with the mobile device 104, may store and retrieve the contact data. Upon retrieving the contact data, the at least one processor 112 may direct the contacts module 114*a* to store the contact data in a structured format. In an example, the structured format may include but may not be limited to the name, phone number, email address, and other relevant data associated with the patient 108, in the memory 114.

The memory 114 may ensure that the contact data is kept secure and accessible for future use. In certain embodiments, the memory 114 may be a non-volatile storage, such as flash memory, ensuring that the contact data persists even when the mobile device 104 is powered off. The contact data may be organized in a way that facilitates easy retrieval, enabling the mobile device 104 to quickly retrieve and utilize the contact data for communication purposes. For example, the stored contact may be used to initiate communication with an associated contact and may further be sent to the remote server 106 for processing or verification.

In some embodiments, the contact data may be associated with the remote server 106. When the mobile device 104 stores the contact data, the at least one processor 112 may be configured to establish a connection between the contact and the mobile device 104. The remote server 106 may send notifications to the mobile device 104, managing communications between the remote server 106 and the mobile device 104, or updating health-related records of the patient 108. Additionally, the contact data stored in the memory 114 may be synchronized with the remote server 106. The synchronization of the contact data may ensure that any changes made to the contact data are reflected across both the mobile device 104 and the remote server 106.

The remote server 106 may send the one or more communications to the patient 108 via any of but not limited to text, email, or other messaging formats. The one or more communications may include, but is not limited to, reminders, health alerts, and other critical updates related to the patient health. In some embodiments, the one or more communications are indicative of being received from the stored contact in the memory 114 of the mobile device 104. The synchronization of the contact data with the remote server 106 may also ensure that all interactions between the remote server 106 and the patient 108 are properly logged and recorded in the remote server 106. For example, the remote server 106 may verify that the contact data is accurate and updated before initiating communication or transferring the patient data to the mobile device 104.

In some embodiments, the at least one processor 112 may further be configured to display an authorization form to the patient 108. The authorization form may be displayed at the display 116 associated with the mobile device 104. Additionally, the at least one processor 112 may be configured to receive one or more user inputs from the patient 108 corresponding to the authorization form. The one or more inputs are given by the patient 108 to depict consent to receiving the one or more communications from the remote server 106. The one or more inputs may include selecting a 'Yes' option or a 'No' option to depict the consent of the patient 108. Further, the at least one processor 112 may be configured to transmit the authorization form to the remote server 106 in response to the receiving the one or more inputs from the patient 108.

In an alternate embodiment, the fitter 110 may obtain a signature of the patient 108 on a paper authorization form similar to the above described authorization form, instead of displaying the authorization form at the display 116 of the mobile device 104. The application may be configured to prompt the patient 108 to capture or photograph the signed authorization form, which the application then uploads to the remote server 106 (e.g., Kestra CareStation platform). In another alternate embodiment, the patient 108 may sign an Email and Texting Authorization Form in DocuSign to provide the consent to receiving the one or more communications from the remote server 106.

In some embodiments, the fitter 110 may upload the signed authorization form of the patient 108 into the application for receiving the one or more communications from the remote server 106. In some embodiments that use Salesforce as the remote server 106 and FSL, the fitter 110 may then upload the signed authorization form for receiving messages or texts into Salesforce using the FSL application. In accordance with embodiments, Salesforce is configured to respond to receiving the authorization from FSL by automatically sending a "welcome message" to the patient 108. In alternate embodiments, instead of uploading the signed authorization, the fitter 110 may provide a copy of the authorization form to the patient 108 to read. If the patient 108 agrees to receive texts from the added contact (e.g., Kestra), the fitter 110 may then use the application (e.g., FSL) to enter into the remote server 106 (e.g., Salesforce) that the patient 108 has received a copy of the authorization form and has agreed to receive messages or texts.

As explained earlier, the fitter 110 may assist the patient 108 in downloading the application in the mobile device 104 and launching the application to provide training on how to use the application. In an exemplary embodiment, the application may be configured to provide a "click through" prompt to the patient 108 for acceptance of the authorization. The application may be further be configured to upload the accepted authorization form to the remote server 106.

In some embodiments, the remote server 106 may include a database for keeping a record of patients 108 registered with the medical system 100. The remote server 106 may further be configured to verify the authenticity of the patient 108 registered into the remote server 106. The verification of the patient 108 may include checking whether the patient data, the contact data, health data, and other personal identifiers associated with the patient 108, are legitimate in accordance with the recorded patient data within the database of the remote server 106. Additionally, the verification of the patient 108 may include adding the patient 108 to the holding clinic. The holding clinic may further serve as a provisional step, allowing the patient data to be maintained and accessed while the physician is designated to oversee the patient 108. The holding clinic may allow the physician to monitor and track health status of the patient 108, even when the physician is not assigned.

In some embodiments, the physician may be assigned to the patient 108 to provide medical advice, and manage ongoing health monitoring of the physiological parameters through the WMD 102. In an example, the physician may be any of but is not limited to a cardiologist, a general practitioner (GP), an emergency medicine physician, an electro physicist, or a general physician assistant. The physician may interpret the patient data collected by the WMD 102, such as but not limited to heart rate, blood pressure, and any detected cardiac conditions.

In some embodiments, the physician may transmit the authorization (discussed above) of the patient 108 to the remote server 106. The remote server 106 may further be configured to receive the authorization through a medical personnel device associated with the physician. The medical personnel device may be any of but is not limited to a tablet, mobile phone, or any other portable device equipped with a software that enables the physician to enter or validate the authorization electronically. The authorization may also ensure that the physician has reviewed the patient data, including the health information, contact details, and any specific instructions regarding the WMD 102.

In some embodiments, the remote server 106 may further authenticate the identity of the physician before accepting and storing the transmitted authorization. The authentication of the physician may involve using, any of but not limited to, unique login credentials, biometric identification, or other security measures to verify that the authorization comes directly from the assigned or legitimate physician.

Upon receiving the transmitted authorization, the remote server 106 may update a patient profile to indicate that the consent of the patient 108 has been granted. The updated patient profile may allow the physician to access the patient data and oversee ongoing treatment plans. Additionally, the medical system 100 may notify the patient 108 about the successful transmission of the authorization, ensuring transparency.

Additionally, the remote server 106 may be configured to transmit the one or more communications to the mobile device 104 in response to receiving the authorization. In some embodiments, the one or more communications are indicative of being received from the stored contact at the mobile device 104. The one or more communications may include, but are not limited to, a welcome message displayed on the display 116 of the mobile device 104 with the contact data associated with the patient 108 or the physician. In an exemplary embodiment, the welcome message may confirm successful receipt of the authorization and welcome the patient 108 to the medical system 100. The welcome message may also include a prompt requesting the patient 108 to reply with "Y" (Yes) or "N" (No) to indicate acceptance of the authorization terms.

Upon receiving "Y" as the reply from the patient 108, the remote server 106 may initiate any of, but not limited to, registration of the patient 108 in the medical system 100 or activation of additional services, ensuring smooth continuation of the patient onboarding process. Thereafter, the remote server 106 may transmit the one or more communications to the mobile device 104. The one or more communications may include any of, but is not limited to, training programs related to the use of the WMD 102, updates corresponding to the patient data, messages from the physician, and other information necessary for care of the patient 108 and interaction with the medical system 100. The one or more communications may ensure the patient 108 is informed of the progress of the patient onboarding process and prepared to engage with the medical system 100.

Figure 2:
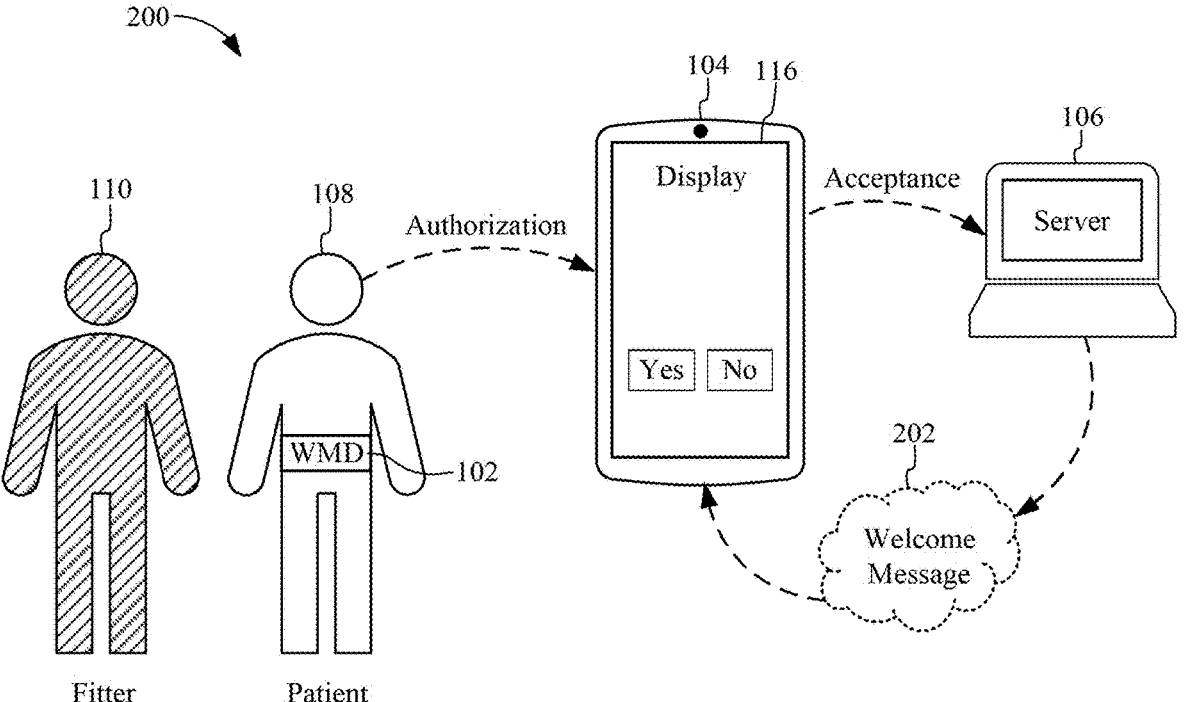
FIG. 2 depicts an example scenario for receiving authorization and consent of a patient to receive one or more communications from the server, according to an embodiment of the present disclosure.

FIG. 2 depicts an example scenario 200 for receiving authorization and consent of the patient 108 to receive one or more communications from the remote server 106, according to an embodiment of the present disclosure. FIG. 2 is described in conjunction with the description of FIG. 1. As shown, FIG. 2 includes the communication flow between the patient 108, the fitter 110, the mobile device 104, and the remote server 106.

In the scenario 200, the fitter 110 may interact with the mobile device 104 while assisting the patient 108. In an exemplary embodiment, the fitter 110 may provide the authorization form to the patient 108 for receiving consent of the patient 108 to receive the one or more communications from the remote server 106. In another exemplary embodiment, the remote server 106 may generate the authorization form at the mobile device 104 for receiving the consent of the patient 108. The authorization form may be generated by the remote server 106 once the patient 108 installs the application into the mobile device 104.

As described previously, the fitter 110 may help the patient 108 understand terms the conditions of the authorization form and the WMD 102 before receiving the consent of the patient 108. Additionally, the terms and conditions of the WMD 102 include, but may not be limited to, collection of health data, monitoring, and the transmission of this data to healthcare providers or other parties.

In some embodiments, the patient 108 may view the authorization form through the display 116 of the mobile device 104. The display 116 may provide a 'Yes' option and a 'No' option to the patient 108 on the authorization form in order to receive the consent of the patient 108. The at least one processor 112 of the mobile device 104 may receive one or more inputs from the patient 108. In an example, the one or more inputs may include choosing any of the 'Yes' or the 'No' option. The 'Yes' or 'No' option may correspond to an approval or refusal to receiving the one or more communications from the remote server 106.

The one or more inputs may instantly be stored in the memory 114 of the mobile device 104 upon receiving either the 'Yes' or the 'No' option. The mobile device 104 may automatically upload the accepted authorization form to the remote server 106 when the patient 108 selects the 'Yes' option. In some embodiments, the transmission of authorization may convey any of, but not limited to, the patient's identity, a consent date, and metadata associated with the consent of the patient 108. The remote server 106 may process the consent data and store the consent data in the database (not shown) of the remote server 106. Once the remote server 106 successfully processes the consent data, the remote server 106 may send a welcome message 202 back to the mobile device 104. In an exemplary embodiment, the Kestra CareStation platform may be configured to verify that the patient 108 is properly added to the Kestra CareStation platform upon receipt of the click-through acceptance. The verification may include adding the patient 108 to the holding clinic if the following physician is yet to be determined by the remote server 106. The Kestra CareStation platform may be configured to communicate the received authorization of the patient 108 to Salesforce upon verification of the patient 108.

The welcome message 202 may indicate that the consent of the patient 108 has been successfully recorded at the remote server 106. The welcome message 202 may further indicate that the patient 108 is now authorized to receive the one or more communications from the remote server 106. The welcome message 202 may further be accompanied with instructions for the patient 108, which may include but is not limited to, guidance on setting up the WMD 102, receiving health alerts, or contacting medical personnel.

In an alternate embodiment, if the patient 108 selects the 'N' option on the authorization form indicating that the patient 108 does not provide consent to receive the one or more communications, the remote server 106 may prompt the patient 108 to provide an explanation. In such a scenario, the mobile device 104 may provide the patient 108 with an option to review the consent form or cancel the authorization process. The mobile device 104 may not transmit any consent data to the remote server 106, and no 'welcome message' may be sent when the patient 108 selects the 'N' option.

Figure 3:
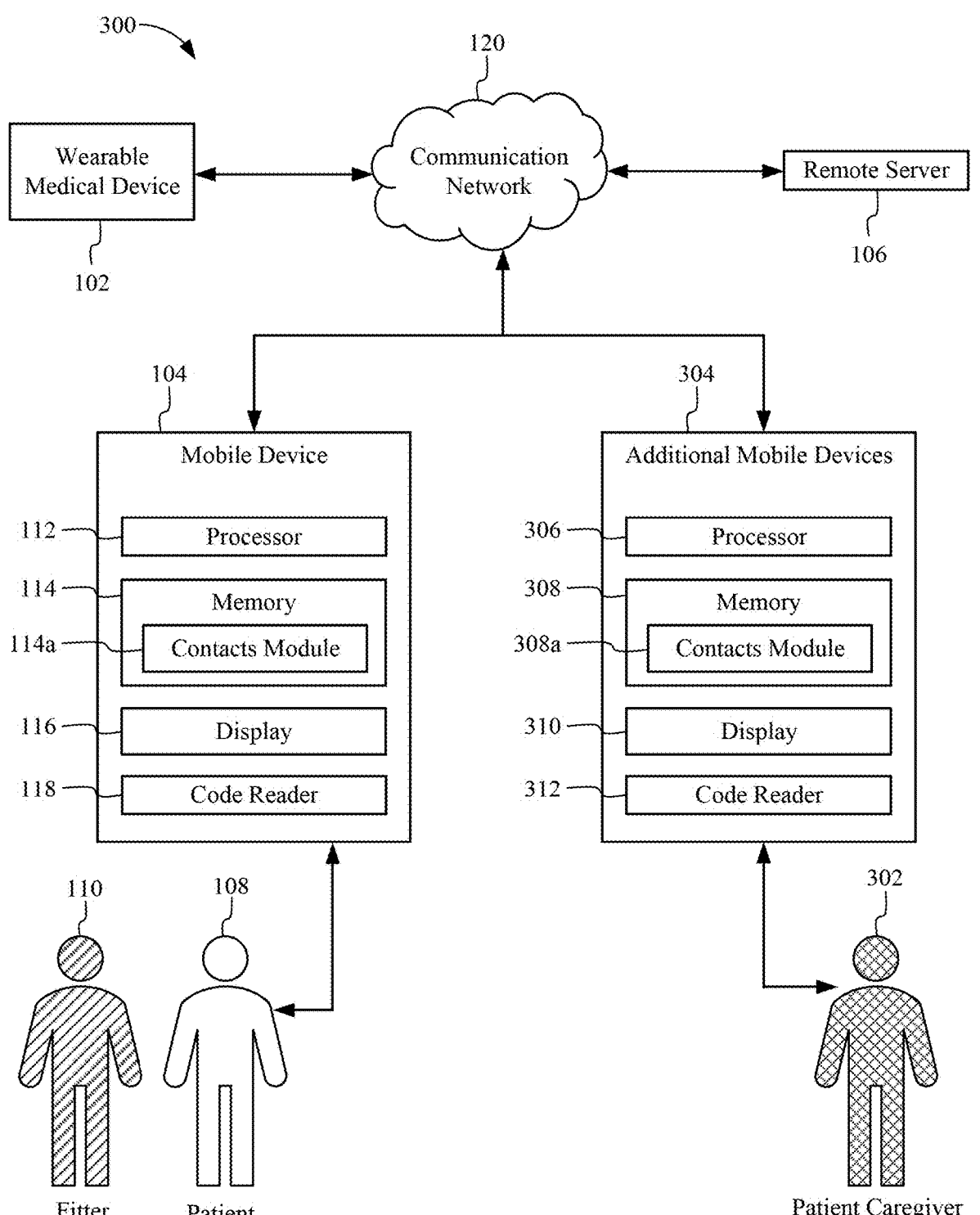
FIG. 3 depicts a medical system for establishing communication between components, in accordance with another embodiment of the present disclosure.

FIG. 3 depicts a medical system 300 for establishing communication between components, in accordance with another embodiment of the present disclosure. FIG. 3 is described in conjunction with the description of previous figures. As described earlier, the medical system 300 includes the WMD 102, the mobile device 104, the remote server 106, the patient 108, and the fitter 110. Additionally, the medical system 300 may include one or more patient caregivers 302 and one or more additional mobile devices 304. As explained in FIG. 1 previously, the mobile device 104 includes the at least one processor 112, the memory 114 including a contacts module 114a, the display 116, and the code reader 118. Additionally, the one or more additional mobile devices 304 may include at least one processor 306, a memory 308 including a contacts module 308a, a display 310, and a code reader 312. The functions of the at least one processor 306, the memory 308, the display 310, and the code reader 312 of the one or more additional mobile devices 304 are similar to those of the at least one processor 112, the memory 114, the display 116, and the code reader 118 of the mobile device 104 described previously. Therefore, the description of similar components are not repeated for the sake brevity. The mobile device 104 and the one or more additional mobile devices 304 are in communication with the remote server 106 via the communication network 120, as well as with the patient 108, the fitter 110, and the one or more patient caregivers 302, for coordination and management of the medical system 300.

In some embodiments, the one or more patient caregivers 302 may include any of but is not limited to, family members, friends, or any other individual related to the patient 108 who may assist the patient 108 with healthcare needs. The one or more patient caregivers 302 may further be responsible for helping the patient 108 with daily tasks, facilitating treatment (e.g., delivery of shock or therapy), and checking whether the WMD 102 is functioning correctly. The one or more patient caregivers 302 may support the patient 108 in understanding and interpreting the patient data accessible through the application on the mobile device 104. Additionally, the one or more patient caregivers 302 may also assist the patient 108 in the management of the mobile device 104 which includes but is not limited to, ensuring the mobile device 104 is properly paired with the WMD 102. The one or more patient caregivers 302 may assist the patient 108 in interactions with the physician.

The one or more patient caregivers 302, similar to the patient 108, may be required to go through the authorization and the QR code verification process as described for the patient 108 in FIG. 1. In some embodiments, the one or more patient caregivers 302 may store the contact data associated with the remote server 106 or the physician in the at least one processor 306 of the one or more additional mobile devices 304. The contact data associated with the remote server 106 or the physician may be stored upon scanning the QR code using the display 310 on the one or more additional mobile devices 304. The contact data may be stored by the contacts module 308a within the one or more additional mobile devices 304. The contact data may further be used to facilitate communication between the one or more patient caregivers 302, the patient 108, and the physician assigned to the patient 108 by the remote server 106. In an embodiment, based on the type and/or severity of the medical condition of the patient 108, a physician or medical professional may be assigned to the patient 108 for reviewing and monitoring the medical condition of the patient 108, and facilitating appropriate treatment to cure the patient 108. As an example, the assigned physician or medical professional may be associated with the maker or provider of the WMD 102, or may be an independent practitioner on a contractual basis.

In an exemplary embodiment, the at least one processor 306 of the one or more additional mobile devices 304 may be configured to receive the code from the fitter 110. In another exemplary embodiment, the at least one processor 306 may be configured to receive the code from the remote server 106 at the display 310. The one or more patient caregivers 302 may install the application at the one or more additional mobile devices 304 to receive the code from the remote server 106. Upon initiating the application, the at least one processor 306 of the one or more additional mobile devices 304 communicates with the remote server 106 over the communication network 120 to retrieve the QR code. Upon receipt of the code, the one or more patient caregivers 302 may scan the QR code and the at least one processor 306 may be configured to process and decode the contact data from the QR code. The contact data may include information associated with contacting the provider or maker of the WMD 102.

In some embodiments, the remote server 106 may be configured to receive the authorization or consent of the one or more patient caregivers 302 to receiving the one or more communications. The remote server 106 may receive the consent from the one or more additional mobile devices 304 once the one or more patient caregivers 302 complete the authorization process. The authorization process may be performed by the one or more patient caregivers 302 in a similar manner to the patient 108 by clicking the 'Yes' option displayed at the display 310 or submitting the authorization form.

The remote server 106 may further initiate communication with the one or more additional mobile devices 304 by transmitting the one or more communications. As discussed for the mobile device 104, the one or more communications sent to the one or more additional mobile devices 304 may include any of but not limited to, a welcome message (e.g., 202), training materials, health data updates, and notifications related to the WMD 102. The one or more communications may ensure that the one or more patient caregivers 302 are properly onboarded into the medical system 300 and are able to support the patient 108. The one or more patient caregivers 302 may use the one or more additional mobile devices 304 to any of, but not limited to, request medical assistance, update the patient health data, or communicate with the fitter 110 or the healthcare provider assigned to the patient 108.

The remote server 106 may further synchronize the contact data stored in the one or more additional mobile devices 304 with the remote server 106. The synchronization may also ensure that any updates or changes made to the contact data at the back-end (e.g., at the remote server 106) may be reflected in both the mobile device 104 and the one or more additional mobile devices 304. The synchronization may further allow seamless communication between the patient 108, the fitter 110, the one or more patient caregivers 302, and healthcare professionals.

FIG. 4 illustrates an example method 400 for establishing communication between a WMD worn by a patient, a mobile device, and one or more remote servers, in accordance with an embodiment of the present disclosure. The method 400 will be explained in conjunction with the description of previous figures. Although the example utilized for the method 400 depicts a particular sequence of operations, the sequence may be altered without departing from the scope of the present disclosure. For example, some of the operations depicted may be performed in parallel or in a different sequence that does not materially affect the function of the method 400. In other examples, different components of an example apparatus or system that implements the method 400 may perform functions at substantially the same time or in a specific sequence.

The method 400 may begin at block 402, by scanning a code including a contact via a code reader of a mobile device. In an embodiment, the patient 108 may receive the code at the mobile device 104 from the remote server 106 when the patient 108 installs and runs the application on the mobile device 104. In an alternate embodiment, the fitter 110 may provide the code to the patient 108. In an example, the code may be a QR code, bar code, or any other encoded format that contains the contact data. In some embodiments, the code reader 118 may include a camera or an optical scanning module present within the mobile device 104 for scanning purpose. In an example, the contact may be associated with a physician, medical professional, or any other member associated with Kestra Medical Technologies Inc. Additionally, the scanned code may contain encoded data, such as, but not limited to, a phone number, email, or other contact details of the physician, medical professional, or any other member associated with Kestra Medical Technologies Inc. The scanned code may allow the mobile device 104 to collect the contact data for communication with the remote server 106.

Further, the method 400, at block 404, includes storing the contact in the memory 114 of the mobile device 104 by the contacts module 114a of the mobile device 104 based on the code. The contacts module 114a may be responsible for organizing and storing the contact data of the contact associated with the remote server 106 once the code is scanned by the patient 108 via the code reader 118 of the mobile device 104. In some embodiments, the contact data may be stored locally in the memory 114 of the mobile device 104. In an alternate embodiment, the contact data may be saved to a cloud-based system associated with the mobile device 104 for easy synchronization across multiple devices of the medical system 100. The stored contact may be accessed later for communication purposes, such as sending messages or making calls.

Further, the method 400, at block 406, includes transmitting an authorization to the remote server 106. In embodiments, the authorization may be transmitted via the mobile device 104 indicating the consent of the patient 108 to receive the one or more communications from the remote server 106. The authorization may verify that the mobile device 104 is authorized to receive or display the one or more communications from the remote server 106. In some embodiments, the process of seeking authorization from the patient 108 may include displaying the authorization form on the display 116 of the mobile device 104. Responsive to displaying the authorization form, the patient 108 may provide one or more inputs via a "click through" type prompt for acceptance of the authorization. The at least one processor 112 of the mobile device 104 may then transmit or upload the accepted authorization form and the patient's acceptance to the remote server 106 (e.g., Kestra CareStation) to provide the required authorization. In an exemplary embodiment, the authorization or the consent from the patient 108 may be obtained by medical personnel, for example, a doctor, a physician, or a healthcare worker, who may approve and transmit the authorization to the remote server 106. The medical personnel may transmit the authorization or acceptance to the remote server 106 from a device owned by the medical personnel.

Subsequent to transmitting the authorization, the method 400, at block 408, includes receiving the one or more communications, at the mobile device 104, from the remote server 106. The one or more communications are indicative of being received from the contact stored in the memory 114 of the mobile device 104, thereby identifying the respective communication as legitimate and not from any spam, scam, or fraudulent contact. In certain embodiments, the one or more communications may include a variety of content such as, but not limited to, a welcome message (e.g., 202), training programs, patient data, physician messages, or other relevant information. In some embodiments, the welcome message 202 may be transmitted or triggered automatically to the mobile device 104 once the authorization from the patient 108 is received by the remote server 106. In an example, the welcome message 202 may contain a greeting or an introductory message related to the contact. Additionally, the one or more communications may also include information associated with the WMD 102, such as any of reminders, alerts, or educational content. Accordingly, the one or more communications received or displayed by the mobile device 104 cause an improvement in the usage of the WMD 102 by the patient 108 based on the type of content included in the one or more communications.

Once the one or more communications are transmitted via the remote server 106 and received by the mobile device 104, the method 400, at block 410, includes displaying the received one or more communications on the display 116 of the mobile device 104. The display 116 may present a variety of different messages, including the welcome message 202 or other communications of the one or more communications related to the contact. The displayed messages may allow a user to interact with the medical system 100 and respond to the one or more communications. In an exemplary embodiment, the user may refer to a person interacting with the mobile device 104, particularly in relation to the scanning of the code and receiving the one or more communications. The user may have a variety of roles depending on the specific use case of the mobile device 104 and the medical system 100.

In an example, the user may be the patient 108 wearing the WMD 102 and using the application to manage patient health. In another example, the user may be the patient who scans the code using the mobile device 104 to pair with the medical system 100. The patient 108 may then receive the one or more communications. As explained above, the patient 108 may then be prompted to provide the consent via the authorization form displayed on the display 116, allowing the mobile device 104 to transmit the patient data securely to the remote server 106. In another example, the user may be a caregiver who may manage the patient's health using the mobile device 104 connected to the WMD 102. In another examples, the user may be any of the medical personnel, a family member, and a new device user.

In some embodiments, the authorization form may be designed to ensure that the user acknowledges and agrees to specific terms of the medical system 100. In additional or alternate embodiments, the method 400 may further include scanning the code via the one or more additional mobile devices 304. In some embodiments, the one or more patient caregivers 302 may scan the code on the WMD 102 to link the one or more additional mobile devices 304 associated with medical system 100. The one or more patient caregivers 302 may receive the authorization form for the one or more additional mobile devices 304 from the remote server 106 to confirm the consent of the one or more patient caregivers 302 for receiving the one or more communications. After submitting the authorization form, the one or more patient caregivers 302 may receive health alerts or updates regarding the patient data on the one or more additional mobile devices 304. In an exemplary embodiment, the one or more additional mobile devices 304 may be used by any of, but not limited to, family members, the one or more patient caregivers 302, or the medical personnel involved in monitoring or assisting the user.

The method 400 may further include displaying the one or more communications on the display 310 of the one or more additional mobile devices 304. Depending on the nature of the one or more communications, the display 310 may be in the form of text notifications, images, graphs, or interactive content. The display 310 of the one or more additional mobile devices 304 may allow the user, whether the caregiver, the family member, or the medical personnel, to review the one or more communications and respond if necessary. The display 310 may also allow the user to interact, such as but not limited to, acknowledging receipt of the patient data, making modifications to the patient data, or forwarding the one or more communications to another party if required.

Therefore, in the various embodiments described, the medical system 100 (or 300) provides a significant improvement in managing patient care by ensuring that the patient 108 receives authorized and legitimate communications from the remote server 106. By utilizing communication between the mobile device 104 and the remote server 106, the medical system 100 allows efficient authorization and consent management, enabling the patient 108 to provide consent for receiving the one or more communications via an interface on the display 116 of the mobile device 104. The aforementioned process guarantees that the patient 108 receives only trusted and pertinent alerts and updates from a legitimate sender, thereby resolving the previous issue where the patient 108 frequently misidentified important medical calls as scams and subsequently canceled them. Further, upon granting consent, the patient 108 receives timely and important updates, health alerts, and critical communications directly from the remote server 106, all of which are securely stored and transmitted. Moreover, the capability to synchronize contact data across multiple devices, including the one or more additional mobile devices 304, increases the flexibility of the medical system 100, ensuring that the one or more patient caregivers 302 and medical professionals are consistently updated and equipped to provide efficient support. This real-time interaction fosters improved coordination in patient care, enhancing the overall healthcare experience and ensuring that the patient 108 is consistently supported by a well-informed network of the one or more patient caregivers 302 and professionals. Additionally, the integration of multiple mobile devices 104 and one or more additional mobile devices 304 ensures that both patients 108 and the one or more patient caregivers 302 are fully integrated into the medical system 100, promoting a collaborative approach to managing patient health.

Other embodiments include combinations and sub-combinations of features described or shown in the drawings herein, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

These and other changes can be made to the embodiments in light of the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

What is claimed is:

1. A medical system comprising:
   a wearable medical device configured to provide therapy to a patient upon detection of a cardiac condition of the patient based on patient data;
   one or more remote servers;
   a mobile device comprising at least one processor, a memory, a display, and a code reader, the mobile device in communication with the one or more remote servers and the wearable medical device, the at least one processor configured to:
      receive a code from the code reader, the code comprising a contact;
      cause the contact to be stored in the memory of the mobile device by a contacts module of the mobile device based on the code,
      wherein the contact comprises contact data, and
      wherein the contact data is associated with the one or more remote servers;
      transmit an authorization to the one or more remote servers; and
      receive, in response to transmitting the authorization, one or more communications at the mobile device from the one or more remote servers, wherein the one or more communications are indicative of being received from the stored contact; and
   one or more additional mobile devices associated with one or more patient caregivers, the one or more additional mobile devices comprising at least one processor, a memory, a display, and a code reader, the at least one processor of the one or more additional mobile devices configured to:
      receive the code from the code reader; and
      cause the contact to be stored in the memory of the one or more additional mobile devices by a contacts module of the one or more additional mobile devices based on the code
      wherein, in response to transmitting an authorization for the one or more additional mobile devices to the one or more remote servers, the at least one processor of the one or more additional mobile devices is configured to receive the one or more communications at the one or more additional mobile devices.

2. The medical system of claim 1, wherein the one or more communications include a welcome message displayed on the display with the contact data.

3. The medical system of claim 1, wherein the code is a Quick Response (QR) code.

4. The medical system of claim 1, wherein the at least one processor is further configured to:
   display an authorization form;
   receive one or more user inputs associated with the authorization form; and
   transmit the authorization form to the one or more remote servers.

5. The medical system of claim 1, wherein the authorization is transmitted to the one or more remote servers by medical personnel using a medical personnel device.

6. The medical system of claim 1, wherein the one or more communications include training programs, patient data, physician messages, and other communications associated with the wearable medical device.

7. A method for establishing communication between a wearable medical device worn by a patient, a mobile device, and one or more remote servers, the method comprising:
   scanning, via a code reader of the mobile device, a code comprising a contact;
   storing the contact in a memory of the mobile device by a contacts module of the mobile device based on the code;
   transmitting, via the mobile device, an authorization to the one or more remote servers;
   receiving, at the mobile device, one or more communications from the one or more remote servers, the one or more communications causing improvement in usage of the wearable medical device by the patient;
   displaying, on a display of the mobile device, the one or more communications;
   scanning, via a code reader of one or more additional mobile devices, the code;
   storing the contact in a memory of the one or more additional mobile devices by a contacts module of the one or more additional mobile devices;
   transmitting, via the one or more additional mobile devices, an authorization for the one or more additional mobile devices to the one or more remote servers;
      receiving, at the one or more additional mobile device, the one or more communications from the one or more remote servers;
   wherein the contact comprises contact data,
   wherein the contact data is associated with the one or more remote servers, and
   wherein the one or more communications include the contact data.

8. The method of claim 7, wherein the received one or more communications include a welcome message, and wherein the welcome message is received automatically upon the transmission of the authorization.

9. The method of claim 7, wherein the code is a QR code.

10. The method of claim 7, wherein transmitting the authorization comprises:
   displaying an authorization form on the display of the mobile device;
   receiving one or more user inputs associated with the authorization form; and
   transmitting the authorization form to the one or more remote servers.

11. The method of claim 7, wherein the authorization is transmitted to the one or more remote servers by medical personnel using a medical personnel device.

12. The method of claim 7, wherein the one or more communications include training programs, patient data, physician messages, and other communications associated with the wearable medical device.

13. The method of claim 7, further comprising:
   displaying, on a display of the one or more additional mobile devices, the one or more communications.

14. A non-transitory computer readable medium, encoded with instructions stored thereon for establishing communication between a wearable medical device, a mobile device, and one or more remote servers, that when executed by at least one computing device causes the at least one computing device to perform operations for establishing communication between the wearable medical device, the mobile device, and the one or more remote servers, the operations comprising:

receiving, via a code reader of the mobile device, a code comprising a contact;

storing the contact in a memory of the mobile device by a contacts module of the mobile device based on the code;

transmitting, via the mobile device, an authorization to the one or more remote servers;

receiving, at the mobile device, one or more communications to the mobile device from the one or more remote servers, the one or more communications causing improvement in usage of the wearable medical device by a patient;

displaying, on a display of the mobile device, the one or more communications;

scanning, via a code reader of one or more additional mobile devices, the code;

storing the contact in a memory of the one or more additional mobile devices by a contacts module of the one or more additional mobile devices;

transmitting, via the one or more additional mobile devices, an authorization to the one or more remote servers; and receiving, at the one or more additional mobile devices, the one or more communications from the one or more remote servers;

wherein the contact comprises contact data, wherein the contact data is associated with the one or more remote servers, and wherein the one or more communications include the contact data.

15. The non-transitory computer readable medium of claim 14, wherein the one or more communications include a welcome message, and wherein the welcome message is transmitted automatically upon receipt of the authorization.

16. The non-transitory computer readable medium of claim 14, wherein transmitting the authorization comprises:

displaying an authorization form on the display of the mobile device;

receiving one or more user inputs associated with the authorization form; and transmitting the authorization form to the one or more remote servers.

17. The non-transitory computer readable medium of claim 14, wherein the one or more communications include training programs, patient data, physician messages, and other communications associated with the wearable medical device.

18. The non-transitory computer readable medium of claim 14, the operations further comprising:

displaying, on a display of the one or more additional mobile devices, the one or more communications.

* * * * *